(12) United States Patent
Ahlen et al.

(10) Patent No.: US 6,334,773 B1
(45) Date of Patent: Jan. 1, 2002

(54) METHOD AND ARRANGEMENT FOR MAKING ARTIFICIAL TEETH

(75) Inventors: Hans Ahlen, Stockholm; Leif Ek, Bandhagen; Gustav Wolrath, Solna, all of (SE)

(73) Assignee: Dentronic AB, Skelleftea (SE)

( * ) Notice: Subject to any disclaimer, the term of this patent is extended or adjusted under 35 U.S.C. 154(b) by 0 days.

(21) Appl. No.: 09/367,973
(22) PCT Filed: Feb. 24, 1998
(86) PCT No.: PCT/SE98/00323
§ 371 Date: Jan. 28, 2000
§ 102(e) Date: Jan. 28, 2000
(87) PCT Pub. No.: WO98/36702
PCT Pub. Date: Aug. 27, 1998

(30) Foreign Application Priority Data

Feb. 24, 1997 (SE) ................................. 9700634

(51) Int. Cl.[7] .............................. A61C 1/00; A61C 3/00
(52) U.S. Cl. .......................................... 433/29; 433/215
(58) Field of Search .................... 433/29, 223, 215, 433/229

(56) References Cited

U.S. PATENT DOCUMENTS

| | | | |
|---|---|---|---|
| 4,486,842 A | * 12/1984 | Hermann | 364/513 |
| 4,663,720 A | * 5/1987 | Duret et al. | |
| 5,101,442 A | * 3/1992 | Amir | 382/41 |
| 5,376,796 A | * 12/1994 | Chan et al. | 250/363.04 |
| 5,383,752 A | * 1/1995 | Rheinberger et al. | |
| 5,440,496 A | * 8/1995 | Andersson et al. | |
| 5,870,220 A | * 2/1999 | Migdal et al. | 359/216 |

FOREIGN PATENT DOCUMENTS

| | | | |
|---|---|---|---|
| CA | A12057337 | * | 6/1992 |
| EP | A10054785 | * | 4/1981 |
| EP | A20299490 | * | 1/1989 |

OTHER PUBLICATIONS

Duret, Francois et al., CAD–CAM in Dentistry, *JADA*, vol. 117, Nov. 1988, pp. 715–720.*

Duret, Francois, "Vers Une Prothese Informatisee," *Tonus*, No. 73, Nov. 30, 1985, pp. 55–57.*

Leinfelder, Karl F., et al., "A New Method for Generating Ceramic Restorations: a CAD–CAM System," *JADA*, vol. 118, Jun. 1989, pp. 703–707.*

* cited by examiner

*Primary Examiner*—Nicholas D. Lucchesi
(74) *Attorney, Agent, or Firm*—Birch, Stewart Kolasch & Birch, LL

(57) ABSTRACT

A procedure and an arrangement for determining a three dimensional shape of a dental object includes the steps of providing a laser, a matrix of photo-detectors, and a controller; scanning a first narrow laser beam from the laser across a first surface area of the dental object; reflecting the first narrow laser beam away from the object; receiving a first scanning image of the reflected first narrow laser beam on the matrix of photo-detectors; determining first elevation profile data based upon the first scanning image relating to the first surface area; changing a relative angle between the laser, matrix of photo-detectors or dental object; scanning a second narrow laser beam from the laser across a second surface area of the dental object; reflecting the second narrow laser beam away from the object; receiving a second scanning image of the reflected second narrow laser beam on the matrix of photo-detectors; determining second elevation profile data based upon the second scanning image relating to the second surface area; and consolidating the first elevation profile data and the second elevation profile data to determine a three dimensional shape of the dental object.

18 Claims, 1 Drawing Sheet ically planar laser beam for illuminating an object with a narrow
METHOD AND ARRANGEMENT FOR MAKING ARTIFICIAL TEETH This application is the national phase under 35 U.S.C. §371 of PCT International Application No. PCT/SE00323 which has an International filling date of Feb. 24, 1998, which designated the United States of America.

BACKGROUND OF THE INVENTION

1. Field of the Invention

The present invention relates to a method and an apparatus for the remote determination of three-dimensional shapes of dental objects, such as teeth, casts of teeth and models of teeth.

2. Description of the Background Art

A current trend in dental care is a desired to stop performing restoration procedures, involving shaping materials such as amalgam and plastic, directly in the mouth. Instead, the trend is to develop or shape materials outside of the mouth. Such shaping outside the mouth can occur by die casting, spark machining, abrasive machining or similar acts.

In order to shape materials outside the mouth, or for that matter inside the mouth, it is important to determine an accurate three-dimensional shape of the dental object being replaced or restored. By determining the shape of a dental object, such as a drilled-out tooth, in three dimensions, a suitably adapted restoration insert, such as a filling, can be produced to fit the object. There is also an increased need for the three dimensional shape of the dental object to be made more accurately and remotely.

An arrangement for producing dental inserts that uses a mechanical means to transfer the shape from an impression of the tooth to a machining tool is known. The accuracy of the shape of such an insert is, however, often too low to achieve a reliable repair.

U.S. Pat. No. 4,964,770 shows an arrangement for producing an artificial tooth where the stump of the tooth is illuminated by a strip of wide light and where a camera is arranged to scan-in the illuminated stump of the tooth. When the scanned-in information is processed, the intensity of light at the lines and along their lengths constitutes an important factor for determining the shape of the stump of the tooth.

Determination of shape can either take place directly in the mouth, from a cast impression or from a model. During optical input of natural teeth directly in the oral cavity, the measurements are impaired by saliva, and other optical imperfections on the surface of the tooth, such as different shades of color, etc. The accuracy of inputting the three-dimensional shape is, therefore, sometimes too low, which can lead to the fit of the insert being poor. For these reasons, it is still preferable when using known techniques to carry out the measurement outside of the oral cavity. During measurement, it is often sufficient to determine the shape of the surface to which the restoration body is to be adapted. Under certain conditions, however, it is also desirable to measure adjacently and oppositely located teeth.

SUMMARY OF THE INVENTION

Accordingly, it is a primary object of the present invention to provide a method and apparatus for the remote determination of a three-dimensional shape of dental objects, such as teeth, casts of teeth and models of teeth.

Another object of the present invention is to provide a method and apparatus which can determined a three-dimensional shape more accurately and more cost effectively than the existing methods and apparatuses.

These and other objects of the present invention are fulfilled by providing a method for determining a three dimensional shape of a dental object comprising the steps of: providing a laser, a matrix of photo-detectors, and a controller; scanning a first narrow laser beam from the laser across a first surface area of the dental object; reflecting the first narrow laser beam away from the object; receiving a first scanning image of the reflected first narrow laser beam on the matrix of photo-detectors; determining first elevation profile data based upon the first scanning image relating to the first surface area; changing a relative angle between the laser, matrix of photo-detectors or dental object; scanning a second narrow laser beam from the laser across a second surface area of the dental object; reflecting the second narrow laser beam away from the object; receiving a second scanning image of the reflected second narrow laser beam on the matrix of photo-detectors; determining second elevation profile data based upon the second scanning image relating to the second surface area; and consolidating the first elevation profile data and the second elevation profile data to determine a three dimensional shape of the dental object.

Moreover, these and other objects of the present invention are fulfilled by providing an apparatus for determining a three dimensional shape of a dental object comprising: a transmission unit, including a laser, producing an essentially planar laser beam for illuminating an object with a narrow laser beam trace; a receiver unit arranged at a distance and to a side of said transmission unit, said receiver unit including a photo-detector matrix for receiving the laser beam reflected from the object; and a calculation unit connected to said photo-detector matrix calculating a three dimensional shape of the dental object based upon the reflected laser beam received by the photo-detector matrix.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
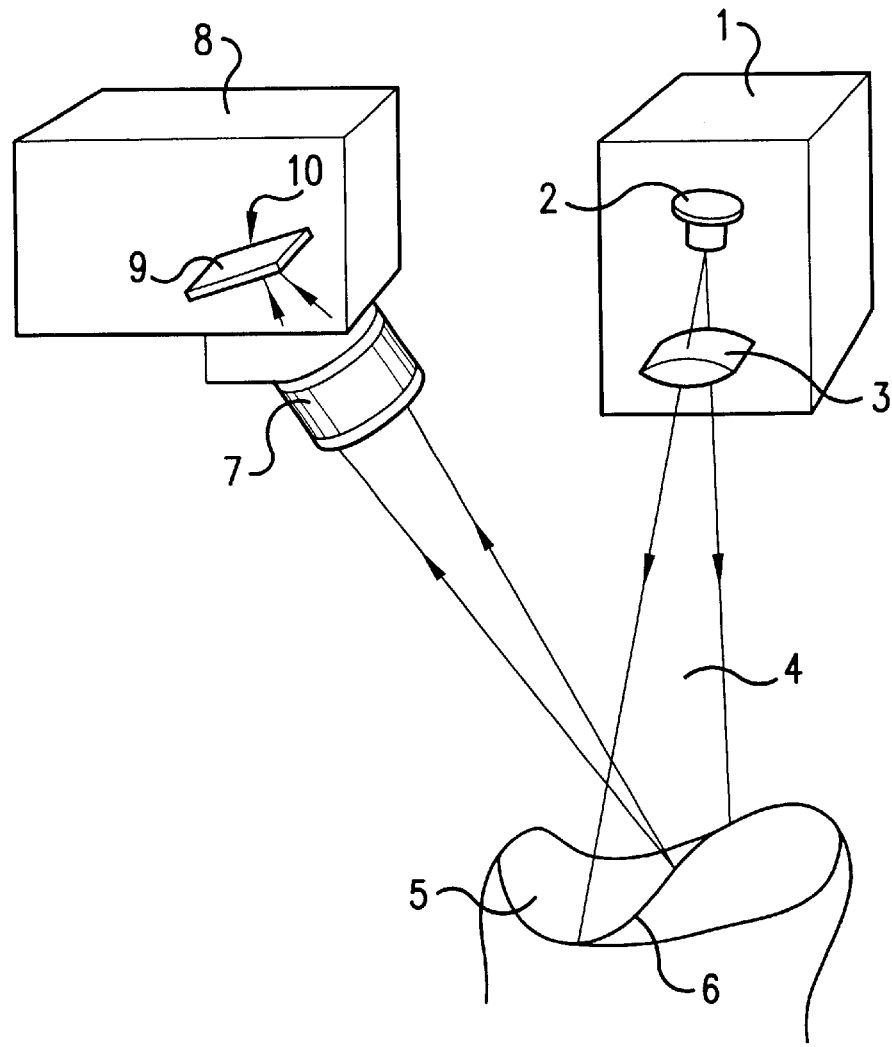
FIG. 1 is a schematic illustration of a layout of an apparatus for determining a three dimensional shape of an object, according to the present invention.
Figure 2:
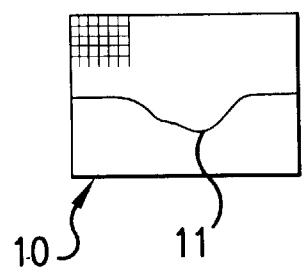
FIG. 2 illustrates a laser trace image on a photo-detector matrix.

Referring in detail to the drawings and with particular reference to FIG. 1, a transmitter unit 1 includes a laser 2 and transmission optics 3. The transmitter unit 1 generates an essentially planar, or disc-shaped, laser projection 4. The laser projection 4 generates a narrow laser trace 6, in the shape of an illuminated line, when it strikes the object to be measured 5. The narrow laser trace 6 may be approximately 0.1 mm wide and long enough to cover the surface of the object under evaluation.

Part of the light scattered or reflected from the object to be measured 5 is picked up by a camera unit 8 that has its optical axis arranged at an angle to the transmitter unit's optical plane defined by the laser projection 4. The angle is preferably less than 60 degrees. It has been determined that an angle of 10 to 45 degrees is beneficial, with an angle of 22.5 degrees being especially desirable. A larger angle gives a scan with greater accuracy, but at the same time, the risk that surrounding variations in the surface levels will get in the way of the illuminated portions of the surface increases.

The camera unit 8 includes an optical receiver 7 that images the laser trace 6 on a matrix of photo-detectors 9. By imaging the trace from the side at a known angle to the laser projection 4, differences in elevation on the illuminated surface can be discerned or imaged since the curve of the trace corresponds to variations in elevation along the surface. The matrix of photo-detectors 9 is arranged at an angle to the optical axis of the optical receiver 7. This results in the laser trace being presented as a sharp image over the whole matrix of photo-detectors 9 and good accuracy being obtained irrespective of where in the matrix of detectors 9 that the laser trace strikes.

The width of the trace, in other words the width of the laser projection 4, and the distance between the scans determines the resolution. A narrower trace 6 and a shorter distance between scans increases the accuracy.

The elevation profile along the laser trace 6 is determined from the position of an image 11 of the trace impacting on a detection matrix 10. Scanning of the laser trace across the object may occur by traversing the object to be measured 5 across the laser trace 6. Elevation profile data for the whole of the surface of the object to be measured 5 can be obtained.

A number of positions on the surface to be measured 5 can be shadowed because of the angle between the transmitter unit 1 and the camera unit 8. Therefore, the object to be measured 5 has only one surface scanned by the laser trace, and then is rotated by a known angle around a known axis, after which a new reading of elevation profile data takes place. This procedure is repeated in fixed steps, until all parts of the surface of the object to be measured 5 have been registered under favorable conditions/angles.

It is important to note that only the relative positions between the object to be measured 5 and the transmitter unit 1 and camera unit 8 need change. This change can occur by rotating the object to be measured 5, or by rotating the transmitter unit 1 and camera unit 8.

Measurement data collected from the different perspectives is consolidated in a calculation unit, such as a computer, by means of which the complete three-dimensional shape of the object to be measured 5 (in this example, just the upper surface) can be described. The calculation unit employs well-known geometrical algorithms via software or hardwire to determine the three dimensional shape. Further, the calculation unit filters out measurement data that has been collected under unfavorable condition/angles, such as close to the limits or edges of the surface of the object to be measured 5 for a particular scan, where the surface being scanned has partially blocked the transmitting or receiving path of the laser trace, or combinations of these conditions.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for the registration of a three-dimensional shape of a dental object, comprising the following steps:
   a) sweeping the dental object with a laser plane generating a narrow illuminated line on the object;
   b) at regular intervals as the illuminated line moves across the object, imaging the illuminated line by means of a camera that has its optical axis at an angle to the optical plane of the laser beam, wherein the illuminated line is imaged on a matrix including a plurality of rows and columns of photo-detectors;
   c) determining for each image of the illuminated line an elevation profile along the line; and
   d) calculating, on the basis of said elevation profiles, the three-dimensional shape of at least part of the object.

2. A method according to claim 1, further comprising the steps, performed after step c), of
   at least once, rotating the object to a new position relative to the laser beam and thereafter repeating steps a)–c).

3. A method according to claim 1, wherein the sweep of the laser beam over the object to be measured takes place in discontinuous steps between each elevation profile.

4. A method according to claim 3, wherein the three-dimensional shape along the line is determined from the elevation profiles using triangulation algorithms.

5. A method according to claim 1, wherein the sweep of the laser beam over the object to be measured takes place in discontinuous steps between each elevation profile.

6. A method according to claim 1, wherein the three-dimensional shape along the line is determined from the elevation profiles using triangulation algorithms.

7. A method according to claim 1, wherein said plurality of rows and columns of photo-detectors are linearly arranged.

8. An arrangement for the registration of a three-dimensional shape of a dental object, said arrangement comprising: a transmitter unit, a receiver unit and a calculation unit, said transmitter unit including a laser beam generator arranged to generate a narrow illuminated line over the object, and said receiver unit being arranged at an angle from the optical axis of the laser beam to register the illuminated line at regular intervals, wherein said calculation unit is arranged to receive registration data from said receiver unit about at least one elevation profile of the illuminated line and to calculate the three-dimensional shape of the object based on the elevation profile, wherein said receiver unit comprises a matrix including a plurality of rows and columns of photo-detectors for registering the illuminated line.

9. An arrangement according to claim 7, further comprising a rotator for rotating the dental object to predetermined positions relative to said laser beam generator.

10. An arrangement according to claim 8, wherein said matrix of photo-detectors and the means for calculating the elevation profiles are implemented on a same chip.

11. An arrangement according to claim 10, wherein said laser beam generator is arranged to sweep the laser beam over the object in discontinuous steps.

12. An arrangement according to claim 11, wherein said calculation unit is arranged to determine the three-dimensional shape using triangulation algorithms.

13. An arrangement according to claim 12, wherein said laser beam generator is a diode-type laser and said receiver unit includes receiving optics arranged with their optical axis at an imaging angle $\alpha$ to the projection of the laser, said imaging angle being less than 60°.

14. An arrangement according to claim 8, wherein said matrix of photo-detectors and the means for calculating the elevation profiles are implemented on a same chip.

15. An arrangement according to claim 8, wherein said laser beam generator is arranged to sweep the laser beam over the object in discontinuous steps.

16. An arrangement according to claim 8, wherein said calculation unit is arranged to determine the three-dimensional shape using triangulation algorithms.

17. An arrangement according to claim 8, wherein said laser beam generator is a diode-type laser and said receiver unit includes receiving optics arranged with their optical axis at an imaging angle $\alpha$ to the projection of the laser, said imaging angle being less 60°.

18. An arrangement according to claim 8, wherein said plurality of rows and columns of photo-detectors are linearly arranged.

* * * * *